(12) United States Patent
Atiqullah et al.

(10) Patent No.: US 9,836,584 B2
(45) Date of Patent: Dec. 5, 2017

(54) METHOD OF QUANTITATIVE DETERMINATION OF NONISOTHERMAL THERMOOXIDATIVE DEGRATION EFFECTS OF A POLYOLEFIN MATERIAL COMPRISING A RESIDUAL CATALYST

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventors: Muhammad Atiqullah, Dhahran (SA); Mohammad Mozahar Hossain, Dhahran (SA)

(73) Assignees: King Fahd University of Petroleum and Minerals, Dhahran (SA); King Abdulaziz City of Science and Technology, Riyadh (SA)

( * ) Notice: Subject to any disclaimer, the term of this patent is extended or adjusted under 35 U.S.C. 154(b) by 1012 days.

(21) Appl. No.: 14/144,216

(22) Filed: Dec. 30, 2013

(65) Prior Publication Data

US 2015/0186620 A1 Jul. 2, 2015

(51) Int. Cl.
*G06F 17/10* (2006.01)
*G06F 19/00* (2011.01)

(52) U.S. Cl.
CPC .................................. *G06F 19/702* (2013.01)

(58) Field of Classification Search
None
See application file for complete search history.

(56) References Cited

U.S. PATENT DOCUMENTS

| | | | |
|---|---|---|---|
| 6,723,805 | B2 | 4/2004 | Braganca et al. |
| 7,402,635 | B2 | 7/2008 | Noll |
| 2007/0106059 | A1* | 5/2007 | Cholli .................. C07C 235/38 528/422 |

FOREIGN PATENT DOCUMENTS

CN 101842394 A 9/2010

OTHER PUBLICATIONS

Belmontes et al. Therno-Oxidative Degradation of HDPE as a Function of Its Crystalline Content Journal of Polymer Science: Part B: Polymer Physics, vol. 47, pp. 1906-1915, 2009.*
Atiqullah et al. Apparent Kinetics of Nonisothermal High Temperature Oxidative Degradation of Ethylene Homopolymers: Effects of Residual Catalyst Surface Chemistry and Structure J Polymer Res 20:56, Jan. 2013.*
Hussain et al. Polymer Degradation and Stability Polymer Degradation and Stability 95, 2010, pp. 2289-2299.*
Polyolefin—Wikipedia en.wikipedia.org/wiki/Polyolefin, pp. 1-2, Jan. 6, 2017.*

(Continued)

*Primary Examiner* — Omar Fernandez Rivas
*Assistant Examiner* — Cuong Luu
(74) *Attorney, Agent, or Firm* — Oblon, McClelland, Maier & Neustadt, L.L.P.

(57) ABSTRACT

A method for quantitative determination of nonisothermal thermooxidative degradation effects of a polyolefin material containing a residual catalyst. The method includes determining a first thermooxidative degradation by obtaining a thermogravimetric analysis spectrum of polyolefin, and then modifying the first thermooxidative degradation based on a structure of the residual catalyst to obtain final thermooxidative degradation properties of the polyolefin.

10 Claims, 3 Drawing Sheets

(56) References Cited

OTHER PUBLICATIONS

Chiovetta and Estenoz, "Ethylene Polymerization With Supported Metallocene Catalysts: Predictions Using a Cube-Cell Model," $2^{nd}$ Mercosur Congress on Chemical Engineering $4^{th}$ Mercosur Congress on Process Systems Engineering, 2005, 10 pages.

Budrugeac, "Applicability of non-isothermal model-free predictions for assessment of conversion vs. time for complex processes in isothermal and quasi-isothermal conditions," Thermochimica Acta, vol. 558, 20, Apr. 2013, pp. 67-73.

Quevedo-Sanchez et al., "Kinetic Modeling of the Effect of MAO/Zr Ration and Chain Transfer to Aluminum in Zirconocene Catalyzed Propylene Polymerization," Macromolecules 2006, 39, pp. 4306-4316.

Podolan et al., "Olefin Polymerization With Supported Metallocene Catalysts," $12^{th}$ Bratsilava International IUPAC/EPF Conference on Polymers Proceedings, Aug. 1997.

* cited by examiner

METHOD OF QUANTITATIVE DETERMINATION OF NONISOTHERMAL THERMOOXIDATIVE DEGRATION EFFECTS OF A POLYOLEFIN MATERIAL COMPRISING A RESIDUAL CATALYST

BACKGROUND OF THE INVENTION

Field of the Disclosure

The present invention relates to method for the quantitative determination of nonisothermal thermooxidative degradation effects of a polyolefin material comprising a residual catalyst. The method utilizes thermogravimetric analysis (TGA) and mathematical modeling with a rigorous constitutive kinetic model.

Description of Related Art

Ethylene homopolymers are commercially produced using supported Ziegler-Natta, chrome, and metallocene catalysts. The as-synthesized catalysts disintegrate during polymerization, architect the molecular structures of the polymer backbones, and develop the desired particulate resin morphology (Webb S W, Weist E L, Chiovetta M G, Laurence R L, Conner W C (1991) The Can J Chem Eng 69:665-681; Grof Z, Kosek J, Marek M (2005) AIChE J 51:2048-2067; Zheng X, Smit M, Chadwick J C, Loos J (2005) Macromolecules 38:4673-4678; Martino A D, Broyer J P, Spitz R, Weickert G, McKenna T F L (2005) Macromol Rapid Commun 26:215-220; Martino A D, Weickert G, Sidoroff F, McKenna T F L (2007) Macromol React Eng 1:38-352; Silva F M, Broyer J P, Novat C, Lima E L, Pinto J C, McKenna T F L (2005) Macromol React Eng 16:1846-1853; Atiqullah M, Akhtar M N, Moman A, Abu-Raqabah A H, Palackal S J, Al-Muallem H A, Hamed O M (2007) Appl. Catal. A: General 320:134-143; Atiqullah M, Moman A, Akhtar M N, Al-Muallem H A, Abu-Raqabah A H, Neaz A (2007) J Appl Poly Sci 106:3149-3157—incorporated by reference in its entirety). The homopolymer molecular structures are characterized by molecular weight distributions (polydispersity index) and their averages, and side chain branching (if any). The following factors—support type, catalyst precursors, and the surface chemistry and structure of the as-synthesized catalyst—affect the morphology and molecular structures of the resulting polymers.

After polymerization, the as-synthesized catalysts remain as residues in the final polymer. Being present in trace amounts, the residual catalysts are not recovered and recycled. Therefore, they become an integral part of the matrix of the synthesized polymer, and eventually they affect polymer processing, as well as applications and properties of the end-products. The concentration and distribution of the residual catalysts depend on the support type, catalyst activity, and polymerization process types and reaction conditions.

Figure 1:
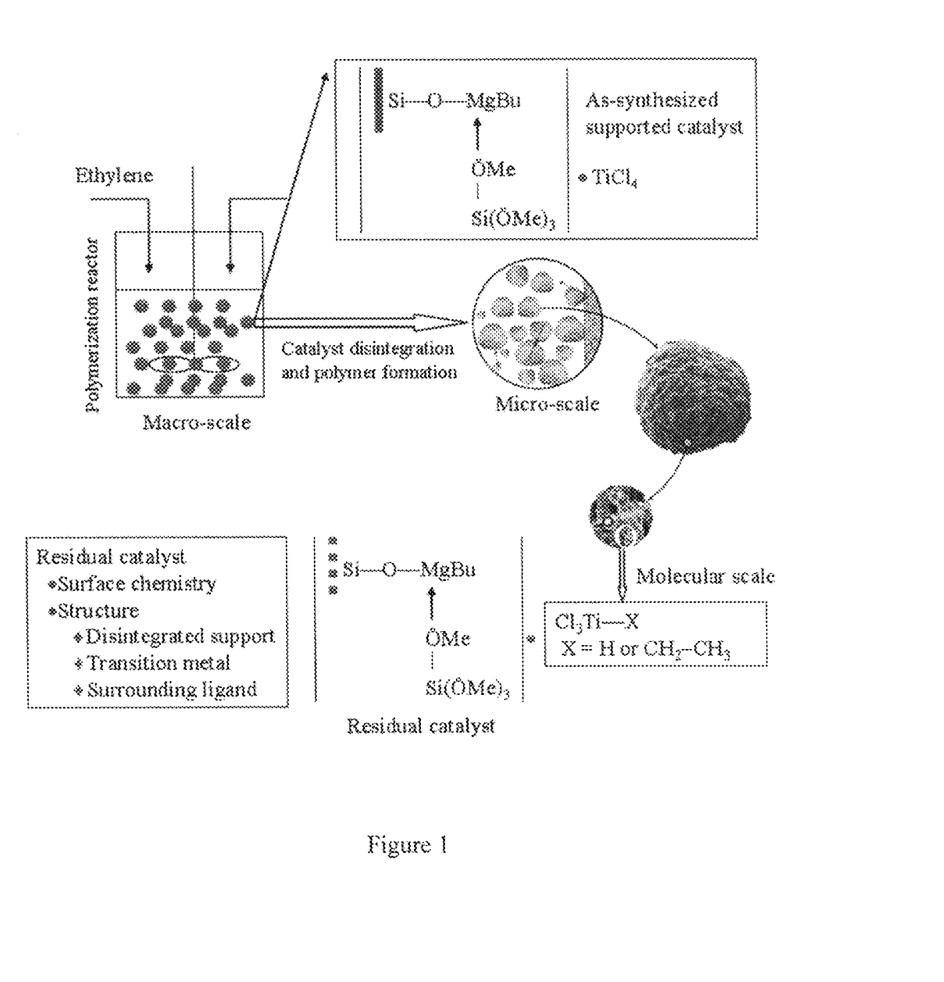
FIG. 1 is a diagram of the genesis of surface chemistry and structure of a supported residual catalyst.

FIG. 1 illustrates how the disintegration of a supported catalyst particle generates the residual catalysts through macro-scale to micro-scale to molecular-scale events. The residual catalysts are functionalized molecular entity (Dompazis G, Kanellopoulos V, Chatzidoukas C, Kiparissides C (2005) Proceedings, 3$^{rd}$ European Conference on the Reaction Engineering of Polyolefins, Lyon, June 20-24, France— incorporated by reference in its entirety), and differ in surface chemistry and structure from the corresponding as-synthesized catalysts. Residual catalysts structure as used herein refers to the catalyst transition metal, combined with the surrounding ligands including the disintegrated support. The metal center experiences electronic and steric effects due to its Lewis acidity (electron density) and the characteristic configuration of the surrounding ligands (Lee I-M, Gauthier W J, Ball J M., Iyengar B., Collins S (1992) Organometallics 11:2115-2122; Rappé A K, Skiff W M, Casewit C J, (2000) Chem Rev 100:1435-1456; Atiqullah M, Akhtar M N, Faiz M, Moman A, Abu-Raqabah A H, Khan J H, Wazeer M I (2006) Surf Inter Anal 38:1319-1327; Kong Y, Yi J, Dou X, Liu W, Huang Q, Gao K, Yang W (2010) Polymer 51:3859-3866—incorporated by reference in its entirety).

The ethylene homopolymers, including HDPEs, have a large number of applications. Therefore, in recent years, the production and consumption of these thermoplastics have significantly increased. This is a boon. However, what is bad is that they are flammable; they hardly degrade in the ambient atmosphere. Consequently, they are an obnoxious source of environmental pollution, causing littering and accumulation in the municipal solid waste. Hence, it is a subject of serious ecological concern and issue (Camacho W, Karlsson S (2002) Polym Degrad Stab 78:385-391— incorporated by reference in its entirety). Stringent legislations are, therefore, being developed worldwide to effectively address these problems. Conversion of the post-use polyolefin thermoplastic end-products into value-added hydrocarbons is being practiced as a prospective solution. Therefore, research continues in this area that involves catalytic cracking of commercial polyolefin resins (Marcilla A, Hernández M D R, García Á N (2007) J Anal Appl Pyrol 79:424-432; Fernandes V J, Araujo A S, Fernandes G J T (1999) J Ther Anal Calorim 56:275-285; Uemichi Y, Kashiwaya Y, Ayame A, Kanoh H (1984) Chem Lett 1:41-44; Uemichi Y, Kashiwaya Y, Tsukidate M, Ayame A, Kanoh H (1983) Bull Chem Soc Jpn 56:2768-2773—incorporated by reference in its entirety).

To the best of our knowledge, the role of residual catalysts, especially in the high temperature thermooxidative degradation of ethylene homopolymers, has not yet been studied even though this can provide important information on material behavior under more realistic atmospheric conditions. The average diameter of residual catalyst particles may be in the order of 100 nm (Ben G S, Goss H, Nakatani, Graeme A, Georgeb M, Terano (2003) Polym Degrad Stab 82: 119-126—incorporated by reference in its entirety). Consequently, they are likely to interact on a molecular level with the polymer backbones. Hence, they may act as a source of temperature-resistant heterogeneous catalytic moiety, and consequently interfere into the overall thermooxidative degradation process.

To study the role of the residual catalysts in high temperature thermooxidative degradation is a pre-requisite to fully understanding catalytic cracking of polyolefins.

BRIEF SUMMARY

An objective of the invention is a method for quantitative determination of nonisothermal thermooxidative degradation effects of a polyolefin material comprising a residual catalyst.

In one embodiment of the invention, the method comprises determining a first thermooxidative degradation by obtaining a thermogravimetric analysis spectrum of polyolefin, and then modifying the first thermooxidative degradation based on a structure of the residual catalyst to obtain final thermooxidative degradation properties of the polyolefin.

In another embodiment the method utilizes a rigorous constitutive kinetic model.

In another embodiment of the invention the rigorous constitutive kinetic model uses a formula in which $T_0$ is a centering temperature that resides around the mean temperature range of the reaction.

In one aspect of the invention the method determines degradation of ethylene homopolymers synthesized using a Ziegler-Natta catalyst.

In another aspect of the invention the method determines degradation of ethylene homopolymers synthesized using a metallocene catalyst.

BRIEF DESCRIPTION OF THE DRAWINGS

FIG. 3 is a plot of $$\ln\left(\frac{1-W_{fraction}^{1-n}}{1-n}\right)$$

as a function of $\Theta/T_{max}$ passing through the origin.

DETAILED DESCRIPTION

In the present disclosure, several subjects such as the development of catalysts, mechanism of cracking, kinetic modeling, and process and product development are investigated for two ethylene homopolymers one synthesized using a Ziegler-Natta (Z-N) catalyst and the other by a metallocene one (each supported on silica). Both catalysts are prepared and characterized. Hence, the surface chemistry and structure of the as-synthesized catalysts and those of the residual catalysts are known, and they significantly vary from each other. The homopolymer samples are made using a laboratory-scale reactor under comparable polymerization conditions to minimize the effects of varying hydrodynamics on polymer morphology. The following aspects of polymer analysis are included in the disclosure:
  i. Elucidation of as-synthesized versus the residual catalyst surface chemistry and structure;
  ii. Determination of the influence of the variation in the types of the surface chemistry and structure of the as-synthesized catalysts on the molecular properties and morphology of a polyolefin;
  iii. Determination of the kinetics and mechanism of the nonisothermal high temperature oxidative degradation of the synthesized ethylene homopolymers using thermogravimetric analysis (TGA) experiments and lumped mathematical modeling;
  iv. Correlation of the performance of the simplified Horowitz and Metzger analytical model (Horowitz H H, Metzger G (1963) Analy Chem 35:1464-1468—incorporated by reference in its entirety) with that of the newly developed rigorous constitutive kinetic model to predict polymer degradation characteristics; and
  v. Correlation of the effects of the types of the residual catalyst surface chemistry and structure with model predictions and degradation mechanism to predict polymer degradation properties.

Polymer degradation properties can be determined or predicted by a quasi-analytical method. Another quasi-analytical model that approximates the temperature integral $$\int \exp\left(-\frac{E_a}{RT}\right)dT -$$

where $E_a$ is the apparent activation energy, R is the universal gas constant, and T is the absolute temperature.

A major focus of the present disclosure is to (i) correlate a unified molecular level concept of characteristic surface chemistry and structure of the residual catalysts to a degradation process, and (ii) determine the apparent kinetics of thermooxidative degradation to predict polymer properties. A single heating rate model-fitting approach may be applied (considering the degradation as a defined process).

To model, correlate, and/or predict the high temperature nonisothermal oxidative degradation of polymers, the selection of the appropriate basis is important. The desired model correlation and/or prediction should:
  Appropriately accommodate the molecular level description of the residual catalyst with its characteristic surface chemistry and structure;
  Regenerate the experimental TGA thermogram;
  Conform to the heterogeneous thermooxidative polymer degradation mechanism all throughout the transformation process;
  Reflect the invariance of lumped/overall reaction order and apparent kinetic energy with respect to fractional weight loss of the polymer; and
  Be easy to experiment, implement, and use.

Thus, a single heating rate TGA experimental approach is used (Horowitz H H, Metzger G (1963) Analy Chem 35:1464-1468; Van Krevelen D W, van Herden C, Huntjens F J (1951) Fuel:30, 253; Coats A W, Redfern J P (1964) Nature 201:68-69; Gonzales J, Albano C, Sciamanna R, Ichazo M, Rosales C, Martinez J (2000) Polym Degrad Stab 68:9-19; Gao Z, Amasaki I, Kaneko T, Nakada M (2003) Polym Degrad Stab 81:125-130; Gao Z, Amasaki I, Nakada M (2003) J Anal Appl Pyrol 67:1-9; Orfão JJM (2007) AIChE J 53:2905-2915; Farjas J, Roura P (2008) AIChE J 54:2145-2154—incorporated by reference in its entirety), which can adequately estimate the apparent kinetic parameters. Then, the formulation of the following models are analyzed:
  The Horowitz and Metzger analytical linear model (Horowitz H H, Metzger G (1963) Analy Chem 35:1464-1468—incorporated by reference in its entirety).
  The rigorous constitutive kinetic model, which is herein disclosed.

One model, correlation or prediction type includes a Horowitz and Metzger analytical linear model. Assuming that the high temperature nonisothermal degradation of a polymer is a function of temperature and the fractional amount of the remnant solid, the overall rate of degradation r can be expressed as follows.

$$r = \frac{dW_{fraction}}{dt} = k(T) \times f(W_{fraction}) \quad (1)$$

where $W_{fraction}$ is the post-degradation weight fraction of the sample; t is the time; k(T) is the temperature-dependent rate constant; and $f(W_{fraction})$ is a kinetic function that relates to the involved degradation mechanism.

Using the Arrhenius expression for k(T), and assuming the power-law model for $f(W_{fraction})$ (Mampel K L (1940) Zeitschrift für Physikalische Chemie 187:235-249; Senum G I, Yang R T (1977) J Therm Anal 11 (3):445-447—incorporated by reference in its entirety), Equation 1 can be written as:

$$r = \frac{dW_{fraction}}{dt} = -Z\exp\left(-\frac{E_a}{RT}\right)W_{fraction}^n \quad (2)$$

where R is universal gas constant; T is absolute temperature (in K); $E_a$ is the apparent activation energy; Z is the frequency factor; and n is the overall order of degradation. Note that the frequency factor Z represents the steric hindrance of degradation that originates from the combined effects of (i) residual catalyst concentration, surface chemistry, and structure; and (ii) the $M_w$ and PDI of the polymer sample.

In a typical TGA experimental run, a constant heating rate q=dT/dt is used. Therefore, Equation 2 reduces to:

$$\frac{dW_{fraction}}{dT} = -Z/q\exp\left(-\frac{E_a}{RT}\right)W_{fraction}^n \quad (3)$$

Upon the assumption that the degradation mostly occurs over a narrow temperature range around $T_{max}$, corresponding to which $$\frac{dW_{fraction}}{dT}$$

is maximum and $$\frac{d^2W_{fraction}}{dT^2} = 0;$$

and considering that the temperature integral $$\int \exp\left(-\frac{E_a}{RT}\right)dt$$

can be approximated by $$-\frac{RT_{max}^2}{E_a}\exp\left[-\frac{E_a}{RT_{max}}\left(1-\frac{\Theta}{T_{max}}\right)\right]$$

$$\left(\text{where } T - T_{max} = \Theta, \text{ and } \frac{\Theta}{T_{max}} \ll 1\right),$$

obtaining the following final equations (Horowitz H H, Metzger G (1963) Analy Chem 35:1464-1468—incorporated by reference in its entirety). Note that the retention of the first two terms of the Taylor series expansion of $$\left(1 + \frac{\Theta}{T_{max}}\right)^{-1},$$

corresponding to $$\frac{\Theta}{T_{max}} \ll 1,$$

leads to the above approximation. The above first and second derivatives are readily generated by the software of a standard TGA instrument.

For a first order degradation, that is, n=1:

$$\ln\{-\ln(W_{fraction})\} = \frac{E_a}{RT_{max}} \times \frac{\Theta}{T_{max}} \quad (4)$$

For a non-first order degradation, that is, n≠1:

$$\ln\left(\frac{1 - W_{fraction}^{1-n}}{1-n}\right) = \frac{E_a}{RT_{max}} \times \frac{\Theta}{T_{max}} \quad (5)$$

Equations 4 and 5 show that plotting the left hand side as a function of $$\frac{\Theta}{T_{max}}$$

should give a straight line, with a slope equal to $$\frac{E_a}{RT_{max}},$$

that passes through the origin. In either case, $E_a$ can be calculated from the slope. The solution to the first order degradation is straightforward. However, for the non-first order case (n≠1), iterate as follows:

Step 1: Assume n;
Step 2: Calculate the left hand side of Equation 4, taking points around the origin (Θ=0) that satisfy $$\left|\frac{\Theta}{T_{max}}\right| \ll 1;$$

and
Step 3: Draw a straight line (using the above points) such that it passes through the origin and shows a coefficient of determination $R^2 \approx 1$; and
Step 4: Determine $E_a$ from the slope $$\frac{E_a}{RT_{max}}$$

of the above best-fit line drawn in the closest proximity of the origin.

If Step 3 is not satisfied, re-assume n and repeat the calculation.

The validity and performance of the model predictions can be evaluated by calculating $T_{1/2}|_{theo}$ and $W_{fraction}^{max}|_{theo}$ (value at $T_{max}$). Putting $W_{fraction}=0.5$ in Equation 5, to obtain:

$$T_{1/2}|_{theo} = T_{max}\left[1 + \left(\frac{E_a}{RT_{max}}\right)^{-1} \ln\left(\frac{1-0.5^{1-n}}{1-n}\right)\right] \quad (6)$$

$W_{fraction}^{max}|_{theo}$ can be derived by using Equation 2 in conjunction with the fourth Senum and Yang approximation (Routray K, Deo G (2005) AIChE J 51:1733-1746—incorporated by reference in its entirety), the final forms are written as:

$$W_{fraction}^{max}|_{theo} = \exp[-h(x)] \quad n = 1 \quad (7)$$

$$W_{fraction}^{max}|_{theo} = \left[1 - \frac{n-1}{n}h\left(\frac{E_a}{RT_{max}}\right)\right]^{1/(n-1)} \quad n \neq 1 \quad (8)$$

where $h(x) = \dfrac{x^4 + 18x^3 + 86x^2 + 96x}{x^4 + 20x^3 + 120x^2 + 240x + 120}$ $$x = \frac{E_a}{RT_{max}} \text{(slope)} \quad (9)$$

The frequency factor Z is given by the following expression (Horowitz H H, Metzger G (1963) Analy Chem 35:1464-1468—incorporated by reference in its entirety), $$Z = \frac{qW_{frac}^{1-n}}{nT_{max}}\left(\frac{E_a}{RT_{max}}\right)\exp\left(\frac{E_a}{RT_{max}}\right) \quad (10)$$

The disclosure also includes a rigorous constitutive kinetic model, correlation or prediction routine. Following are the inherent limitations of the Horowitz and Metzger model (Horowitz H H, Metzger G (1963) Analy Chem 35:1464-1468—incorporated by reference in its entirety).
  i. The consideration that degradation mostly occurs over a narrow temperature range around $T_{max}$; and
  ii. The approximation of the temperature integral by $$-\frac{RT_{max}^2}{E_a}\exp\left[-\frac{E}{RT_{max}}\left(1 - \frac{\Theta}{T_{max}}\right)\right].$$

Therefore, a rigorous constitutive kinetic model is proposed that can be developed by using the following form of Arrhenius expression $$k = Z\exp\left[\frac{-E_a}{R}\left(\frac{1}{T} - \frac{1}{T_0}\right)\right]$$

in Equation 2 where $T_0$ is the centering temperature, that resides around the mean temperature range of the reaction (Routray K, Deo G (2005) AIChE J 51:1733-1746; Hossain M M, de Lasa H I (2007) AIChE J 53:1817-1829; Fogler H S, (2006). Elements of Chemical Reaction Engineering, 4th Eds, Prentice Hall International, NJ, USA—incorporated by reference in its entirety). This centering procedure facilitates searching the kinetic parameters by minimizing the statistical correlation between activation energy $E_a$ and preexponential factor Z (Watts D G (1994) The Can J Chem Eng 72:701-710—incorporated by reference in its entirety). Therefore, the final rate equation becomes:

$$r = \frac{dW_{fraction}}{dt} = -Z\exp\left[\frac{-E_a}{R}\left(\frac{1}{T} - \frac{1}{T_0}\right)\right]W_{fraction}^n \quad (11)$$

Equation 11 can be solved point-by-point using the experimental TGA curve.

Consequently, the kinetic parameters n, $E_a$, and Z can be numerically determined.

The effects of two supported residual catalysts—one Ziegler-Natta and another metallocene—on the nonisothermal thermooxidative degradation of the resulting polymers are investigated using TGA experiments and kinetic modeling. The rigorous constitutive kinetic model, unlike the analytical Horowitz and Metzger model, fits very well to the entire TGA curve, without distribution of activation energy $E_a$, for n (overall degradation order)=1 for both polymers. Neither n nor $E_a$ vary as a function of fractional weight loss of the polymer. Hence, the proposed unified molecular level concept of surface chemistry and structure of the residual catalysts hold all through the degradation process. The above feature of n and $E_a$ also indicates the suitability of the model formulation and the effectiveness of the parameter-estimation algorithm.

Random polymer chain scission, with the cleavage of the —C—C— and the —O—O— (hydroperoxide) bonds, prevail. The types of residual catalyst surface chemistry and structure vary the bond cleavage process. The metallocene Zr residual catalyst causes more thermooxidative degradation in MetCat HomoPE than what the Ti one does in Z-N HomoPE. The rigorous constitutive model-predicted apparent kinetic energy $E_a$, and frequency factor Z also support this finding. The proposed degradation mechanism suggests that the Zr residual catalyst more (i) decreases the activation energy required to decompose the —C—C— and the —O—O— bonds, and (ii) eliminates β-hydrogen (by the carbonyl functionalities) from the polymer chains. These findings are attributed to the differences in surface chemistry and structure of the residual catalysts. Therefore, the present disclosure presents a rigorous constitutive kinetic model that duly illustrates, correlates, and or incorporates the influence of the characteristic surface chemistry and structure of the residual catalysts on the prediction, determination and/or modeling high temperature oxidative degradation of polyethylenes.

EXAMPLES

Materials

Silica PQ 3030 (from PQ Corporation), having surface area of 322 m$^2$/g, an average pore volume of 3.00 cm$^3$/g, and a pore size of 374 Å, was used as the support.

("BuCp)$_2$ZrCl$_2$ and MAO (30 wt % in toluene) were obtained from Chemtura. The following chemicals—HCl, HF, H$_3$BO$_3$, Al(NO$_3$)$_3$ stock solution in dilute HNO$_3$ (1.0× 10$^3$ mg Al/l), ammoniumhexafluorosilicate (NH$_4$)$_2$SiF$_6$ (1.0×10$^3$ mg Si/l), AlCl$_3$, and ZrCl$_4$ stock solution (1.0×10$^3$ mg Zr/l)—used for determining the elemental composition of the synthesized catalysts, were obtained from BDH.

Analytical grade trimethylaluminum (TMA) (2 M in heptane), dibutylmagnesium (1 M in heptane), toluene, n-hexane (both 99.999% pure), A4 molecular sieve, 2,6-di-tert-butyl-4-methyl phenol (BHT), and 1,2,4 trichlorobenzene (TCB)—all were obtained from Aldrich. Tetramethoxysilane (TMOS) was purchased from Fluka. Acetylene, ethylene, hydrogen, and nitrous oxide (99.999% pure) were procured from Abdullah Hasim, a local vendor.

Synthesis of Catalysts

The metallocene catalyst [PQ 3030/MAO/("BuCp)$_2$ZrCl$_2$] was synthesized following the procedures detailed in earlier publications (Atiqullah M, Akhtar M N, Moman A, Abu-Raqabah A H, Palackal S J, Al-Muallem H A, Hamed O M (2007) Appl. Catal. A: General 320:134-143; Atiqullah M, Moman A, Akhtar M N, Al-Muallem H A, Abu-Raqabah A H, Neaz A (2007) J Appl Poly Sci 106:3149-3157; Atiqullah M, Akhtar M N, Faiz M, Moman A, Abu-Raqabah A H, Khan J H, Wazeer M I (2006) Surf Inter Anal 38:1319-1327 (incorporated by reference in its entirety). The silica (PQ 3030) was dehydroxylated at 250° C. for 4 hours using a Thermocraft furnace equipped with a vertical quartz glass tube, a digital temperature indicator and controller, a gas flow meter, and a vacuum pump. The silica was continuously fluidized using nitrogen. Upon dehydroxylation, it was stored in an inert glove box.

All the manipulations were done under an inert atmosphere of argon using standard Schlenk technique and a glove box. The solvents used (heptane, toluene and iso-pentane) were dried using 4A type molecular sieve.

The synthesis of the Z-N catalyst [PQ Silica/Bu$_2$Mg/TMOS/TiCl$_4$] is summarized as follows. The silica was dehydroxylated (DH) at 600° C. for 6 hr. About 3 g of this DH silica was taken in a Schlenk flask inside a glove box. Then 30 ml of heptane was added to this under an argon environment, and a slurry was made at 55° C. using an oil bath and by magnetic stirring. Next, about 3.00 ml of Bu$_2$Mg (1 M in heptane) was added. The resulting mixture was heated at the above temperature for 60 min. After this, 0.30 ml of TMOS was introduced, and the reaction was continued for 60 min at 55° C. About 0.32 ml TiCl$_4$ was added, and reacted for 60 min. The excess heptane was removed under vacuum using a fritted filter tube. The final catalyst was washed three times, using 10 ml iso-pentane each time. The wet catalyst was dried to free-flowing powder using vacuum drying. The final catalyst was saved in a glove box.

The bulk elemental compositions of the synthesized catalysts were determined in terms of Al, Mg, Ti, and Zr at wave lengths of 309.3, 285.2, 364.3, and 360.1 nm, respectively using atomic absorption (AA) spectroscopy (Perkin Elmer AAnalyst 100). The determination of each element involved two common steps—calibration of the AA spectrometer and preparation of the experimental sample solution. High purity nitrous oxide-acetylene flame was used for the analyses. The analysis procedures available in the literature were followed (Atiqullah M, Akhtar M N, Moman A, Abu-Raqabah A H, Palackal S J, Al-Muallem H A, Hamed O M (2007) Appl. Catal. A: General 320:134-143; Atiqullah M, Moman A, Akhtar M N, Al-Muallem H A, Abu-Raqabah A H, Neaz A (2007) J Appl Poly Sci 106:3149-3157; Atiqullah M, Akhtar M N, Faiz M, Moman A, Abu-Raqabah A H, Khan J H, Wazeer M I (2006) Surf Inter Anal 38:1319-1327; Perkin Elmer (1996) Atomic Absorption Spectroscopy: Analytical Methods: Manual Number 0303-1052, Release D, Connecticut: Norwalk, The Perkin Elmer Corporation—incorporated by reference in its entirety). The catalyst [PQ Silica/Bu$_2$Mg/TMEOS/TiCl$_4$] comprised 1.10 wt % Mg and 4.10 wt % Ti whereas the catalyst [PQ 3030/MAO/("BuCp)$_2$ZrCl$_2$] comprised 18.30 wt % Al and 0.73 wt % Zr.

Ethylene was polymerized using an Imtech laboratory-scale reactor set up. It consisted of a fixed top head and a one-liter jacketed Büchi glass autoclave. The reactor system is detailed in earlier publications (Atiqullah M, Akhtar M N, Moman A, Abu-Raqabah A H, Palackal S J, Al-Muallem H A, Hamed O M (2007) Appl. Catal. A: General 320:134-143; Atiqullah M, Moman A, Akhtar M N, Al-Muallem H A, Abu-Raqabah A H, Neaz A (2007) J Appl Poly Sci 106:3149-3157; Atiqullah M, Akhtar M N, Faiz M, Moman A, Abu-Raqabah A H, Khan J H, Wazeer M I (2006) Surf Inter Anal 38:1319-1327—incorporated by reference in its entirety). The reactor was baked for an hour at about 120° C. Then it was purged with nitrogen four times at about the same temperature.

The metallocene ethylene homopolymer (MetCat HomoPE) was synthesized at 80° C. and 8.0 bar(g) ethylene using the catalyst [PQ 3030/MAO/("BuCp)$_2$ZrCl$_2$]. The trial was continued for 1 hr. The catalyst activity showed to be $2.125 \times 10^4$ kg PE/(mol Zr hr). The Z-N HomoPE was made using the catalyst [PQ 3030/Bu$_2$Mg/TMOS/TiCl$_4$]. The procedure is summarized below.

The reactor was cooled from 120° C. to 55° C. Dried hexane (200 ml) was fed into the reactor. Then 0.5 ml TMA (2 M in heptane) was added. After that about 50 mg of the above catalyst, slurried in 50 ml of dried hexane, was introduced under mild argon pressure into the reactor. All these were completed under purging by argon. Then the reactor was closed. Hydrogen was fed to 2 bar(g); then ethylene was introduced to make the total pressure equal to 10 bar(g). Finally, the temperature was increased and maintained at 80° C. The stirrer speed was 500 rpm. The duration of the polymerization trial was 1 hr. The catalyst activity turned out to be $1.518 \times 10^2$ kg PE/(mol Ti hr).

Characterization of the as-Synthesized Ethylene Homopolymers

Average Molecular Weight and Polydispersity Index

The synthesized Z-N HomoPE and MetCat HomoPE were characterized in terms of molecular properties [weight average molecular weight ($M_W$) and polydispersity index (PDI)] using gel permeation chromatography (GPC) (Polymer Char GPCIR, Spain). Three mixed pore columns (TSK 13 µm, 7.8 mm×30.0 mm) were used.

The antioxidant, 300 ppm 2,6-di-tert-butyl-4-methyl phenol (BHT), was added to 1,2,4 trichlorobenzene (TCB) to prevent the polymer sample from degrading. A sample solution of 1 mg/1 ml (w/v) was prepared at 140° C. in this antioxidant-containing solvent. The resulting solution (200 µl) was injected into the GPC column. The chromatogram data were acquired and analyzed using the Polymer Char GPC1 software. The elution time and flow rate were 40 min and 1.0 ml/min, respectively.

The equipment was first calibrated using polystyrene standards. The resulting calibration curve was converted into the corresponding polyethylene one by multiplying the polystyrene molecular weights with the Q factor (0.436) of NBS1475 PE standard.

Table 1 reports the weight average molecular weight and polydispersity index of the as-synthesized ethylene homopolymers.

TABLE 1

Characteristics of the synthesized ethylene homopolymers.

| Polymer characteristics | Z-N HomoPE | MetCat HomoPE |
|---|---|---|
| Weight average molecular weight ($M_w$) (g/mol) | 402,425 | 115,190 |
| Polydispersity index (PDI) | 7.4 | 2.5 |
| Peak melting point ($T_{pm}$) (° C.) | 136.7 | 120.2 |

TABLE 1-continued

Characteristics of the synthesized ethylene homopolymers.

| Polymer characteristics | Z-N HomoPE | MetCat HomoPE |
|---|---|---|
| Peak crystallization point ($T_{pc}$) (° C.) | 117.8 | 104.0 |
| % crystallinity | 63.0 | 43.0 |
| Surface area (m²/g) | 5.22 | 9.93 |
| Residual catalyst levels (ppm) | | |
| Al | 2,770.0 | 670.0 |
| Mg | 94.1 | |
| Ti | 61.0 | |
| Zr | | 3.5 |
| Si | 931.0 | 2,780.0 |

Thermal properties

The thermal properties of the experimental resins and the films were measured in terms of peak melting point ($T_{pm}$), peak crystallization point ($T_{pc}$), and % crystallinity, using a differential scanning calorimeter (DSC Q2000, Texas Instrument). The instrument was calibrated using indium.

About 4.0±0.2 mg of the sample was put in an aluminum pan, which was tightly closed with a lid. A sealed aluminum pan was used as a reference. The samples and the reference were placed in the experimental carrousel. The samples were heated at 5° C./min from room temperature to 160° C., using a nitrogen flow rate of 50 ml/min (Cycle 1). After this, they were isothermally heated for 5 min to remove the influence of the thermal history, and unmelted crystals that could cause heterogeneous crystallization. Next, it was cooled from 160° C. to −5° C. at the above thermal ramp value (Cycle 2) and was kept at this temperature for 5 min. Finally, the same sample was re-heated at 5° C./min to 160° C. (Cycle 3).

The peak melting temperature ($T_{pm}$) and the % crystallinity were determined from Cycle 3. The thermogram under Cycle 3 fusion endotherm was integrated to measure the heat of fusion ($H_f$) which is proportional to the crystallinity of the polymer. The % crystallinity was calculated from $\Delta H_f(J/g)/\Delta H_{std}(J/g)$, where $\Delta H_{std}$ is the heat of fusion for a perfectly crystalline polyethylene which equals to 290.0 J/g (Islam M A, Hussein I A, Atiqullah M (2007) Eur Polym J 43:599-610—incorporated by reference in its entirety). The peak crystallization temperature ($T_{pc}$) was determined from the Cycle 2 crystallization exotherm. The data for each cycle were acquired and handled using the TA explorer software.

Residual Catalysts in the as-Synthesized Ethylene Homopolymers

The levels of residual catalysts in the as-synthesized resins were determined using inductively coupled plasma (ICP) spectrophotometer [ICP Spectro Ciros Vision, FVE 12-Axial]. The samples (0.10-0.25 g) were placed in a 30 ml platinum (Pt) crucible, and slowly heated first to 200° C.; then to red hot until it was burnt to ash without ignition. The resulting ash was cooled, mixed with 1.00-2.00 g NaOH pellets, and heated, first slowly and then to red hot to produce a transparent melt. This was cooled, acidified with HNO₃ to a pH<2 (to neutralize the alkaline NaOH), filtered, and finally diluted with deionized water for ICP analysis.

The analysis was conducted under the following conditions: RF power (1400 W), argon plasma gas flow (20 l/min), auxiliary gas flow (1.2 l/min), nebulizer gas flow (0.85 l/min), sample uptake rate (2 ml/min), integration time (24 s), and total analysis time (3 min). The data were acquired and analyzed using *Smart Analyzer Vision software*. The following wave lengths, 394.401, 279.553, 334.187, and 343.823 nm, represent Al, Mg, Ti, and Zr, respectively. Table 1 shows the concentrations of these metals found in the experimental polyethylene samples.

The silica content was determined gravimetrically according to ASTM C 114-00 (ASTM Standard 2000).

Surface Area of the as-Synthesized Ethylene Homopolymers

The surface areas of the polymer samples were measured using Autosorb-1 (Quantachrome Instruments, USA). The instrument was first calibrated using alumina having a multipoint BET surface area of 107.66 m²/g. The sample cell, and the polymer samples (about 0.30 g) were degassed for 15 min and 120 min, respectively, at 220° C. under high vacuum to remove the air. The samples were run for 6 hr using liquid nitrogen as the adsorbate. The data were acquired using the software Quantachrome AS1 Win™ and the multi-point BET surface area was calculated from the nitrogen adsorption. The measured surface areas are reported in Table 1.

Nonisothermal High Temperature Oxidative Degradation of the As-Synthesized Ethylene Homopolymers The polymer samples were subject to nonisothermal high temperature oxidative degradation using a TGA instrument (Texas Instrument). About 10 mg of the sample was placed in the sample holder and heated at a rate of 20° C./min from room temperature to 600° C. at ambient air flow. The post-degradation residual weight fraction $$W_{fraction}, \frac{dW_{fraction}}{dT}, \text{ and } \frac{d^2W_{fraction}}{dT^2}$$

were recorded as a function of temperature using the instrument software.

Based on the examples, the disclosure includes:
- Correlating surface chemistry and structure of the as-synthesized versus the residual catalysts as part of predicting polymer degradation;
- Correlating and/or comparing as-synthesized catalyst surface chemistry and structure versus the molecular properties and morphologies of the synthesized ethylene homopolymers as part of predicting polymer degradation;
- Correlating TGA findings and kinetic modeling of oxidative degradation as part of predicting polymer degradation; and
- Determining a mechanism of high temperature oxidative degradation as part of predicting polymer degradation.

Table 2 lists the surface chemistry and structure of the as-synthesized and residual catalysts, which were derived considering the following:

The catalyst characterization and simulation results published in the literature (Dahl I M, Halvorsen S, Slotfeldt-Ellinggsen (1986) J Mol Catal 35:55-63; Pakkanen T T, Vahasarja E, Pakkanen T A, Iiskola E, Sormunen P (1990) J Catal 121:248-261; Nowlin T E, Mink R I, Lo F Y, Kumar T (1991) J Polym Sci: Part A Polym. Chem 29:1167-1173; Kratochvila J, Kadlc Z, Kazda A, Salajka Z (1992) J Non-Crystalline Solids 143:14-20; Kissin Y V, Mink R I, Brandolini A J, Nowlin T E (2009) J Polym Sci Part A: Polym Chem 47:3271-3285; Kissin Y V, Nowlin T E, Mink R I (1993) Macromolecules 26:2151-2158; Cavallo L, Guerra G, Corradini P (1998) J Am Chem Soc 120: 2428-2436; Blitz J P, Diebel R E, Deakyne C A, Christensen J M, Gun'ko V M (2005) J Phy Chem 109:5667-5677; Seth M, Margel P M, Ziegler T (2002) Macromolecules 35:7815-7829; Seth M, Ziegler T (2003) Macromolecules 36:6613-6623; Stukalov D V, Zakharov V A. (2009) J Phy Chem 113:21376-21382—incorporated by reference in its entirety);

The events occurring during catalyst fragmentation and polymerization (FIG. 1); and The mechanism of ethylene polymerization.

TABLE 2

The surface chemistry and structure of the as-synthesized versus residual catalysts.

| Experimental catalysts | As-synthesized catalyst | Residual catalyst |
|---|---|---|
| Z—N catalyst | Si—O—MgBu / ÖMe / MeÖ—Si—ÖMe / ÖMe · \|TiCl$_4$\| | Si—O—MgBu / ÖMe / MeÖ—Si—ÖMe / ÖMe · \|Cl$_2$Ti—X\|, X = H or CH$_2$CH$_3$ |
| Metallocene catalyst | MeAl—, Si—O—Al(O δ⁻)(O δ⁻)—L Zr⁺—Cl$_2$, ClAl—, L = ($^n$BuCp)$_2$ | MeAl—, Si—O—Al(O δ⁻)(O δ⁻)—L Zr⁺—H, ClAl—, L = ($^n$BuCp)$_2$ |

See FIG. 1.

The details of the above derivation are available in earlier publications (Hussain I, Atiqullah M, Fazal A, Alam K, Hossaen A (2010) Polym Degrad Stab 95:2289-2299—incorporated by reference in its entirety). The residual catalysts differ from the corresponding as-synthesized catalysts in terms of particulate dimension, electronic and steric effects, and the ligands surrounding the transition metal center. These characteristic differences eventually represent the variation in the types of heterogeneity between the Ti and Zr residual catalysts. These are distributed into the matrix of the above polymers in 11.68 ppm Ti/(m$^2$/g) [Ti=61.0 ppm, and polymer specific surface area=5.22 m$^2$/g], and 0.35 ppm Zr/(m$^2$/g) [Zr =3.5 ppm, and polymer specific surface area=9.93 m$^2$/g], respectively. See Table 1. In industrial polyethylene samples, the amount of residual catalyst transition metals varies as follows: Ti (0.40-65 ppm), and Zr (0.20-2.00 ppm) (Chirinos-Padrón A J, Hernández P H, Suárez F A (1988) Polym Degrad Stab 20:237-255; Moss S, Zweifel H (1989) Polym Degrad Stab 25:217-245; Hoàng E M, Allen N S, Liauw C M, Fontán E, Lafuente P (2006) Polymer Polym Degrad Stab 91:1356-1362; Allen N S, Fatinikun K O, Henman T J (1983) Eur Polym J 19:551-554; Scheirs J, Bigger S W, Billingham N C (1992) J Polym Sci Part A: Polym Chem 30:1873-1889; Chan J H, Balke S T (1997) Polym Degrad Stab 57:135-149; Mucha M (1976) J Polym Sci Sym. Series 57:25-31; Westerhout R W J, Waanders J, Kuipers J A M, van Swaaij W P M (1997) Ind Eng Chem Res 36:1955-1964; Bockhorn H, Hornung A, Hornung U, Schawaller D (1999) J Anal Appl Pyrol 48:93-109—incorporated by reference in its entirety).

The weight average molecular weight ($M_w$) and polydispersity index (PDI) represent the molecular structures of the as-synthesized ethylene homopolymers. The two catalysts—PQ Silica 3030/Bu$_2$Mg/TMOS/TiCl$_4$ and PQ Silica 3030/MAO/($^n$BuCp)$_2$ZrCl$_2$—were used to synthesize ethylene homopolymers of $M_w$ 402,425 and 115,190 (g/mol); and PDIs 7.4 and 2.5, respectively. See Table 1. Therefore, the Z-N catalyst produced a much higher molecular weight HDPE with a broader PDI. The higher molecular weight is mainly due to the electronic effect introduced by the electron-donating—MeÖ ligand that increased the electron density at the Ti metal center (Kong Y, Yi J, Dou X, Liu W, Huang Q, Gao K, Yang W (2010) Polymer 51:3859-3866—incorporated by reference in its entirety). Consequently, the β-hydrogen elimination and chain transfer to the monomer decreased during ethylene polymerization. The broader PDI results from the multi-site characteristics of the Z-N catalyst. On the other hand, the metallocene catalyst made a typically narrow PDI polymer due to its single-center behavior.

The variation of $M_w$ and PDI also reflects the variation in the rates of initiation, chain growth, and chain termination during polymerization. The differences in surface chemistry and structure of the as-synthesized catalysts implicitly affected the concerned polymerization rates. The ratio of the average rate of chain growth $\dot{r}_{cg}$ to that of chain termination(s) $\dot{r}_{ct}$ can be determined using Equation 12 and the data reported in Table 1 (Kong Y, Yi J, Dou X, Liu W, Huang Q, Gao K, Yang W (2010) Polymer 51:3859-3866—incorporated by reference in its entirety):

$$(\dot{r}_{cg}/\dot{r}_{ct}) = \text{Degree of polymerization} = \frac{M_W}{PDI \times MW_{ethylene}} \quad (12)$$

where $PDI = M_w/M_n$.

As per Equation 12, $(\dot{r}_{cg}/\dot{r}_{ct})_{Z-N\ Cat}:(\dot{r}_{cg}/\dot{r}_{ct})_{MetCat}$=2,080:1,772=1.17:1.00. This relationship elucidates the catalytic influence of reaction rates on the degree of polymerization.

Also analyzed is the high temperature nonisothermal oxidative degradation of the experimental polymers, based on the dynamic TGA experiments; and then, the kinetic modeling of degradation, particularly considering the surface chemistry and structure of the residual catalysts.

Dynamic TGA Findings

Figure 2:
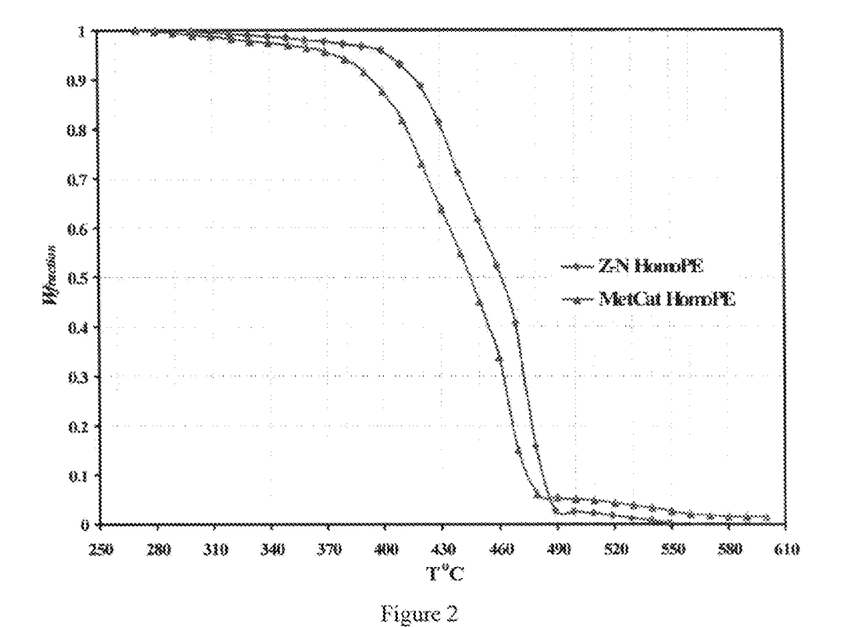
FIG. 2 is a graph of TGA curves of Z-N HomoPE and MetCat HomoPE at a heating rate of 20° C./min.

FIG. 2 compares the dynamic TGA curves of Z-N HomoPE and MetCat HomoPE. The weight of both samples initially decreased slowly as the thermooxidative degradation started; then it decreased sharply over a temperature range of 340 to 490° C. This indicates the formation and evolution of volatile products. Toward the end of degradation, the decrease in weight gradually reduced to about zero. On the other hand, there are several differences. MetCat HomoPE began to lose weight earlier and at lower temperature than Z-N HomoPE, and continued this trend throughout the degradation process. Table 3 lists the temperatures for 50% weight loss ($T_{1/2}$s) and $T_{max}$s for MetCat HomoPE and Z-N HomoPE. $T_{1/2}$ and $T_{max}$ (which qualitatively measure resistance to degradation) of the former were found to be less than those of the latter. Therefore, MetCat HomoPE was found to be more susceptible to thermooxidative degradation than Z-N HomoPE under the same environment of oxygen and temperature.

TABLE 3

Selected experimental parameters, and model predictions related to the high temperature oxidative degradation of ethylene homopolymers.

| Experimental parameters and model predictions | Z-N HomoPE | MetCat HomoPE |
|---|---|---|
| $T_{max}\vert_{experimental}$ (° C.) | 476.87 | 465.44 |
| $T_{1/2}\vert_{experimental}$ (° C.) | 460.10 | 447.00 |
| $T_{1/2}\vert_{theo}$ (° C.) | [1]464.75 | [1]450.04 |
| $W_{fraction}^{max}\vert_{experimental}$ | 0.19 | 0.20 |
| $W_{fraction}^{max}\vert_{theo}$ | [2]0.23 | [2]0.24 |
| Horowitz and Metzger model | | |
| Overall reaction order n | 0.42 | 0.42 |
| Apparent activation energy ($E_a$) (kJ/mol) | 216.35 | 164.19 |
| Frequency factor (Z) (sec$^{-1}$) | $1.64 \times 10^{13}$ | [3]$4.6 \times 10^9$ |
| The proposed rigorous constitutive kinetic model | | |
| Overall reaction order n | 1 | 1 |
| Apparent activation energy ($E_a$) (kJ/mol) | 162 ± 8 | 122 ± 4.4 |
| Frequency factor (Z) (sec$^{-1}$) | $(2.8 \pm 0.1) \times 10^{-3}$ | $(1.2 \pm 0.0) \times 10^{-3}$ |
| Coefficient of determination ($R^2$) | 0.99 | 0.99 |
| Cross-correlation coefficients | 0.89 | 0.78 |

[1,2,3]Calculated using Equations 6, 8, and 10, respectively. The model-predicted kinetic parameters evaluated using the single TGA experiment should be restrictively applied to predict the thermooxidative degradation of polyethylenes in conditions used in this study.

Kinetic Modeling of Oxidative Degradation

Horowitz and Metzger Analytical Linear Model

Figure 3:
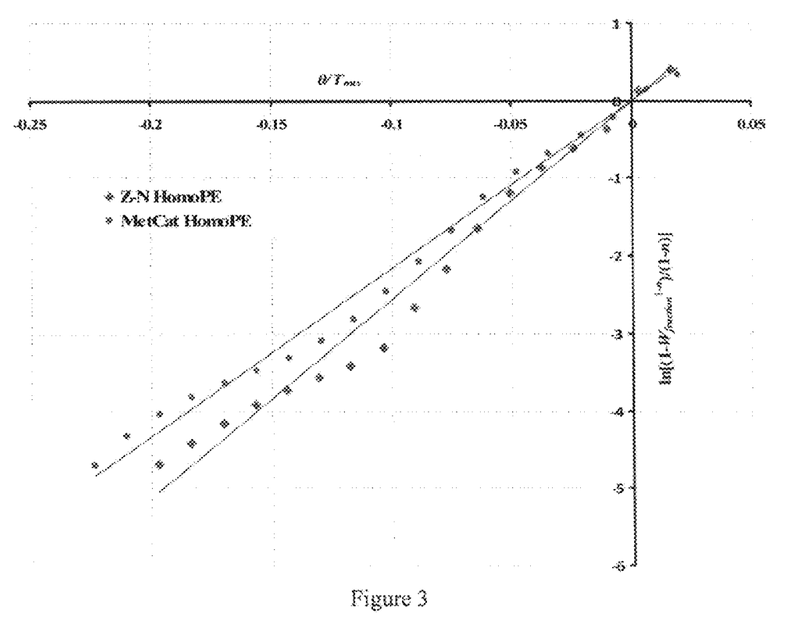

The overall order n and apparent activation energy $E_a$ of degradation were calculated at $T_{max}$, that is, at $$\frac{dW_{fraction}}{dT} = \text{maximum and } \frac{d^2W_{fraction}}{dT^2} = 0,$$

using Equation 5 and Steps 1 to 4 therein. Because of the above constraint, the Horowitz and Metzger model provides a local solution to the problem. The expected relation between these two derivatives, for each polymer sample, was checked using the instrumental software. The $T_{1/2}\vert_{theo}$ and $W_{fraction}^{max}\vert_{theo}$ were calculated using Equations 6 to 9. They are comparable with the corresponding experimental values. See Table 3. FIG. 3, with reference to Equation 5, shows how $$\ln\left(\frac{1-W_{fraction}^{1-n}}{1-n}\right)$$

plotted as a function of $\Theta/T_{max}$ passes through the origin.

Rigorous Constitutive Kinetic Model

The rigorous constitutive model (Equation 11) was evaluated by the least square fitting of the kinetic parameters, using the experimental TGA curve and the MATLAB lsqcurvefit optimization routine. The data points were taken over the entire weight loss range ($W_{fraction}$=0 to 1) to provide a global solution to the problem. Equation 11 was solved using the 4$^{th}$ order Runge-Kutta method (MATLAB ODE 45). During this process, the right hand side was implicitly converted into the temperature integral $$\int \exp\left(-\frac{E_a}{RT}\right)dT,$$

which was subsequently integrated numerically as a function of temperature. The numerical integration of the temperature integral, unlike that in the Horowitz and Metzger model, ensured very high level of accuracy (Órfão J J M (2007) AIChE J 53:2905-2915; Deng C, Cai J, Liu R (2009) Solid State Sci 11:1375-1379—incorporated by reference in its entirety). The centering temperature $T_o$ was taken equal to 725° K to minimize the cross-correlation among the model parameters (Hossain MM, de Lasa HI (2007) AIChE J 53:1817-1829—incorporated by reference in its entirety). The parameters were determined at 95% confidence limit. Twenty-five to thirty (25-30) data points were taken for parameter estimation. Thus, for a given value of n, the degree of freedom for the model exceeded 20 (number of data points—number of parameters to be estimated). This reflects that considerable experimental data were used to iterate the model parameters. This particular feature makes the model predictions more accurate. Convergence was achieved when the model function changed less than the specified tolerance of $10^{-8}$.

The performance of the above model (for different values of n) was assessed based on the following:
  Coefficient of determination ($R^2$);
  Low SSR (sum of the squares of the residuals);
  Low cross-correlation coefficient ($\gamma$); and
  Individual confidence intervals for the model parameters.
  Comparison of Kinetic Model Performance Herein is described first the model predictions with reference to Horowitz and Metzger model (Equation 5); then, the rigorous constitutive kinetic model (Equation 11). In each case, n, $E_a$, and Z will be categorically discussed with their physical significances.

Kinetic Parameters: n, $E_a$, and Z

Figure 4:
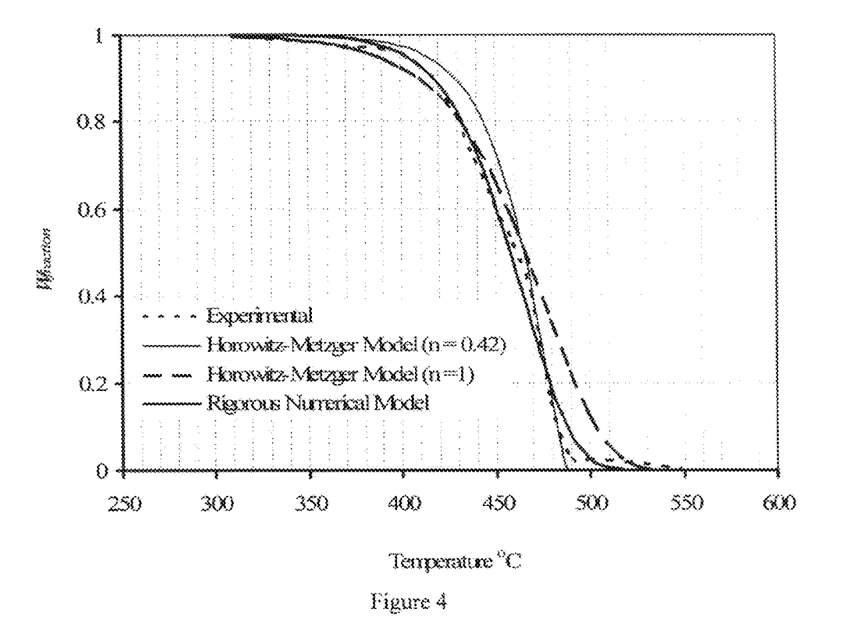
FIG. 4 is a graph showing comparison of experimental versus theoretical plots of $W_{fraction}$ as a function of temperature in TGA experiment for Z-N HomoPE.
Figure 5:
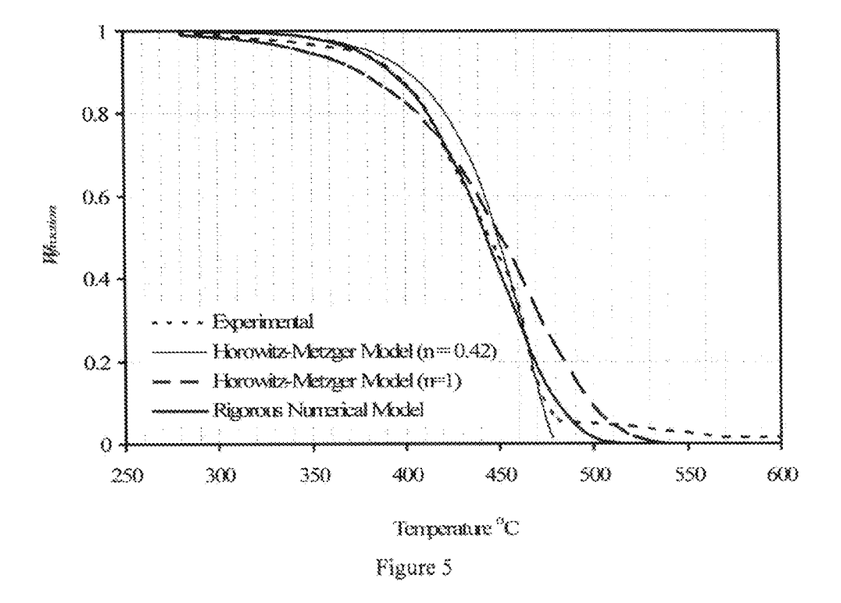
FIG. 5 is a graph showing comparison of experimental versus theoretical plots of $W_{fraction}$ as a function of temperature in TGA experiment for MetCat HomoPE.

FIGS. 4 and 5 show how the Horowitz and Metzger Model results for both polymer samples compare with the corresponding experimental TGA curves. Each figure shows appreciable discrepancy. However, the following is to be noted. Despite differences in polymer sample weight average molecular weight and PDI, the overall order of degradation n turned out to be the same (0.42). The regression coefficients of determination $R^2$ (applicable only at $T_{max}$ and its closest proximity) for the degradation of Z-N HomoPE and MetCat HomoPE are 0.9976 and 0.9967, respectively. The degradation order n=0.42 shows two features. One is that the above polymer properties are probably less limiting above the melting points (120° C., Table 1); and/or the resultant thermal history is lost due to long heating before the onset of degradation. The other is that both samples degraded following the same mechanism. The physical significance of n=0.42 will be reported later on. The Horowitz and Metzger model results were also plotted for n=1. In this particular situation, this model holds only during initiation of the degradation process, corresponding to T=370° C. Beyond this, the model prediction continues to deviate from the experimental TGA curves. The predictions by the rigorous constitutive kinetic model are discussed.

Table 3 lists the estimated $E_a$ and Z for n=1 with $R^2$=0.9999 (which holds for the entire TGA curve). Corresponding to these values, FIGS. 4 and 5 also compare the model-predicted $W_{fraction}$s with the experimental TGA curves for Z-N HomoPE and MetCat HomoPE, respectively. The match, in each case, is excellent. The discrepancy in the fitting exhibited by Horowitz and Metzger model (because of its inherent limitations stated earlier) is now effectively overcome. The intriguing finding is the following. For each ethylene homopolymer, a single value of n and $E_a$ well represents the entire degradation process. Therefore, the unified molecular level concept of surface chemistry and structure of the residual catalysts holds all through the degradation. The application of multiple values of n and $E_a$, which has been reported in the literature (Chan J H, Balke S T (1997) Polym Degrad Stab 57:135-149—incorporated by reference in its entirety), to fit the experimental TGA data, was not necessary. The physical significance of n derived from these two models can be determined as follows.

The overall reaction order n obtained from the Horowitz and Metzger model is less than unity. On the other hand, as per the rigorous constitutive kinetic model, the degradation in each polymer sample followed an overall first-order reaction rate. In the literature, various values of n such as 0.55 (Gao Z, Amasaki I, Kaneko T, Nakada M (2003) Polym Degrad Stab 81:125-130; Gao Z, Amasaki I, Nakada M (2003) J Anal Appl Pyrol 67:1-9—incorporated by reference in its entirety). Therefore, random chain scission predominated in the degradation of both polyethylenes, and this was not affected by the type of residual catalyst surface chemistry and structure. Consequently, the rigorous constitutive kinetic model more correctly concludes the mechanism of degradation. The types of bond cleavage involved in the random chain scission (which yields volatile low molecular weight reaction products) are discussed later.

The apparent activation energy $E_a$ for the thermooxidative degradation of MetCat HomoPE and Z-N HomoPE as per the Horowitz and Metzger model is 164.20 and 216.35 kJ/mol, respectively. However, the rigorous constitutive kinetic model shows these values to be 122±4.4 and 162±8 kJ/mol, respectively. Therefore, in the first instance, these values are overestimated by 1.34 fold; however, the order of variation shows to be the same.

Now $E_a$s are compared with those published in the literature with reference to the cleavage of —C—C— and —O—O— bonds. Both bond cleavages occur in thermooxidative degradation of polyethylenes. The —C—C— cleavage is associated with random chain scission. See Scheme 1 (S1.4, S1.11, and S1.12).

Scheme 1

Proposed sequence of thermal autooxidation, where $R^P$ = polyethylene backbone, $R^POOH$ = polyethylene hydroperoxide, $\Delta$ = thermal energy, and M = residual catalyst.

Chain initiation

Chain propagation

Chain branching: Decomposition of $R^POOH$ by Residual Catalyst

Overall

Chain termination: Disappearance of free radicals (by combination)

Additional degradation products (S1.12)

On the other hand, the —O—O— cleavage results from the limiting monomolecular decomposition of polyethylene hydroperoxide. See Scheme 1 (S1.5 to S1.7) for the details. Hence, this determines the overall kinetics and rate of thermooxidative degradation (Reich L, Stivala S S (1971) Elements of Polymer Degradation, McGraw-Hill, New York; Peterson J D, Vyazovkin S, Wight C A (2001) Macromol Chem Phy 202:775-784—incorporated by reference in its entirety). However, without being assisted by a catalyst, the decomposition of the hydroperoxide requires a relatively high activation energy (200 kJ/mol) which is comparable to the energy of an —O—O— bond scission. In parallel, the activation energy required to cleave the —C—C— bond during thermal degradation of linear polyethylenes has been reported to vary from 262 to 348 kJ/mol (Corrales T, Catalina F, Peinado C, Allen A S, Fontan E (2002) J Photochem Photobiol A: Chem 147:213-224;

Doruker P, Wang Y, Mattice W L (2001) Comp Theoretical Polym Sci 11:155-166; Knyazev V D (2007) J Phy Chem 111:3875-3883; Knûmann R, Bockhorn H. (1994) Comb Sci Tech 101:285-299—incorporated by reference in its entirety).

This disclosure shows that $E_a$ for the thermooxidative degradation of MetCat HomoPE and Z-N HomoPE, predicted by both models, is much less than what has been reported in the literature to cleave the —C—C— and —O—O— bonds. See Table 4 for the details. Therefore, in both samples, the residual catalysts decreased $E_a$; catalyzed these bond cleavages, and enhanced the degradation process. That $E_{a/MetCat\,HomoPE}$ is much less than $E_{a/Z-N\,HomoPE}$ means that the metallocene residual catalyst was more effective in cleaving the —C—C— and —O—O— bonds than the Z-N one. This also substantiates that at high temperatures (340 to 490° C.), MetCat HomoPE, because of the presence of the residual catalyst, is thermooxidatively more degradable than Z-N HomoPE. The susceptibility to the observed degradation turned out to be proportional to $T_{1/2}$ and $T_{max}$ and is inversely related to $E_a$.

TABLE 4

Activation energies reported to cleave the —C—C— bond during thermal degradation of linear polyethylenes.

| Overall activation energy* ($E_a$) (kJ/mol) | Affiliated authors | Ref. |
|---|---|---|
| 285 | Corrales, T.; Catalina, F.; Peinado, C.; Allen, N. S.; Fontan E. (2002). | J Photochem Photobiol A: Chem 147: 213-224 |
| 333 | Doruker, P.; Wang, Y.; Mattice, W. L. (2001) | Comp Theoretical Polym Sci 11: 155-166 |
| 348 | Knyazev, V. D. (2007). | J Phy Chem 111: 3875-3883 |
| 262 | Knumann, R.; Bockhorn, H. (1994) | Comb Sci Tech 101: 285-299 |

*The observed variation is due to using different experimental conditions which are detailed in the corresponding cited references.

The frequency factor Z for the degradation of Z-N HomoPE and MetCat HomoPE, as per the Horowitz and Metzger model (for n=0.42), turned out to be $1.64 \times 10^{13}$ and $4.6 \times 10^9$ sec$^{-1}$, respectively. See Equation 10. On the other hand, the rigorous constitutive kinetic model calculated them to be $(2.8 \pm 0.1) \times 10^{-3}$ and $(1.2 \pm 0.0) \times 10^{-3}$ sec$^{-1}$, respectively. The difference in the estimated Z values by these two models is obviously enormous. Goss et al. evaluated the frequency factor of residual catalyst-aided solid-state heterogenous thermooxidation of as-synthesized polypropylene at 100-150° C., that as well involves the generation of alkoxy radicals, and found this to be even as low as $(3.0-8.0) \times 10^{-8}$ sec$^{-1}$ (Ben G S, Goss H, Nakatani, Graeme A, Georgeb M, Terano (2003) Polym Degrad Stab 82:119-126—incorporated by reference in its entirety).

The above finding has an important significance. Z concerns the entropy of reaction that eventually relates to the involved steric hindrance (among the reactants) (Kim, K. J., Doi, Y., Abe, H (2006) Polym Degrad Stab 91:769-777—incorporated by reference in its entirety). Therefore, Z-N HomoPE ($M_w$=402,425 g/mol; PDI=7.4; Ti=61 ppm) offered more resistance to degradation than MetCat HomoPE (M, =115,190 g/mol; PDI=2.5; Zr =3.5 ppm), which can be ascribed to the combined effects of (i) residual catalyst (transition metal Ti or Zr) concentration, and (ii) the $M_w$ of the polymer sample. Therefore, the model-estimated parameters, particularly $E_a$ and Z are, strictly speaking, aliased function of the residual catalyst (transition metal Ti or Zr) concentration and $M_w$. The former implicitly includes the residual catalyst surface chemistry (representing Lewis acidity effect) and structure. However, this aliased effect does not at all limit the capability of our model and the developed parameter-estimation algorithm. To separate the $M_w$-residual catalyst concentration aliased interaction, a different experimental design may be required.

The apparent kinetic parameters evaluated using the single TGA experiment should be restrictively applied to predict the thermooxidative degradation of polyethylenes in conditions used in this present invention.

Mechanism of High Temperature Oxidative Degradation

The thermooxidative degradation, having basically a free-radical chain mechanism (Gao Z, Amasaki I, Kaneko T, Nakada M (2003) Polym Degrad Stab 81:125-130; Gao Z, Amasaki I, Nakada M (2003) J Anal Appl Pyrol 67:1-9; Chirinos-Padrón A J, Hernández P H, Suárez F A (1988) Polym Degrad Stab 20:237-255; Moss S, Zweifel H (1989) Polym Degrad Stab 25:217-245; Moss S, Zweifel H (1989) Polym Degrad Stab 25:217-245; Corrales T, Catalina F, Peinado C, Allen A S, Fontan E (2002) J Photochem Photobiol A: Chem 147:213-224; Kim, K. J., Doi, Y., Abe, H (2006) Polym Degrad Stab 91:769-777; Gugumus F (1996) Polym Degrad Stab 52:145-157; Gumus F (1997) Polym Degrad Stab 55:21-43; Gumus F (2000) Polym Degrad Stab 68:337-352; Zweifel H, Maier R D, Schiller M (2009) Plastics Additives Handbook, Hanser Verlag, Germany; Osawa Z (1988) Polym Degrad Stab 20:203-236; Lee E O, Kim C Y (1980) Polymer Korea 4:405-412—incorporated by reference in its entirety), is characterized with the following:

i. Cleavage of —C—C— and —O—O— bonds by the residual catalysts; and ii. Predominance of random chain scission.

In the presence of heat, the residual catalysts (Table 2), because of their Lewis acidity, initiated thermooxidation (through oxygen uptake and abstraction of labile hydrogen from the polymer backbone), and produced various radicals, including $R^PO_2\bullet$. See Equation S1.1 of Scheme 1. During chain propagation, $R^PO_2\bullet$ abstracted hydrogen from the polymer backbone and generated polyethylene hydroperoxide. This was subsequently decomposed by the residual catalysts to $R^PO\bullet$ and $R^PO_2\bullet$ at the chain branching step (Gao Z, Amasaki I, Kaneko T, Nakada M (2003) Polym Degrad Stab 81:125-130; Gao Z, Amasaki I, Nakada M (2003) J Anal Appl Pyrol 67:1-9; Chirinos-Padrón A J, Hernández P H, Suárez F A (1988) Polym Degrad Stab 20:237-255; Moss S, Zweifel H (1989) Polym Degrad Stab 25:217-245; Moss S, Zweifel H (1989) Polym Degrad Stab 25:217-245; Corrales T, Catalina F, Peinado C, Allen A S, Fontan E (2002) J Photochem Photobiol A: Chem 147:213-224; Doruker P, Wang Y, Mattice W L (2001) Comp Theoretical Polym Sci 11:155-166; Knyazev V D (2007) J Phy Chem 111:3875-3883; Knûmann R, Bockhorn H. (1994) Comb Sci Tech 101:285-299; Kim, K. J., Doi, Y., Abe, H (2006) Polym Degrad Stab 91:769-777; Gugumus F (1996) Polym Degrad Stab 52:145-157; Gumus F (1997) Polym Degrad Stab 55:21-43; Gumus F (2000) Polym Degrad Stab 68:337-352; Zweifel H, Maier R D, Schiller M (2009) Plastics Additives Handbook, Hanser Verlag, Germany; Osawa Z (1988) Polym Degrad Stab 20:203-236; Lee E O, Kim C Y (1980) Polymer Korea 4:405-412—incorporated by reference in its entirety). See Equations S1.2 to S1.7.

During chain termination, $R^PO_2\bullet$ combined with itself to produce the oxygenated carbonyl groups (carboxyl, ester, ketone, and lactone). These oxygenated products, in the presence of the residual catalysts, are likely to generate additional degradation products through β-hydride elimination from the polymer chains (Kim, K. J., Doi, Y., Abe, H (2006) Polym Degrad Stab 91:769-777—incorporated by reference in its entirety). See Equations S 1.11 and S1.12. Scheme 1 relates to Equation 2 and Equation 11.

Scheme 1, which comprises a sequence of mechanistic elementary reactions, has been proposed to support and explain the model predictions and TGA experiments. Each elementary reaction, being a part of thermooxidative mechanism, is independent of the material basis (mole versus weight) (Rychly J, Matisova-Rychla L, Csmorova K, Achimsky L, Audouin L, Tcharkhtchi A, Verdu J (1997). Polym Degrad Stab 58:269-274—incorporated by reference in its entirety). Therefore, Scheme 1 phenomenologically applies to Equation 2 and Equation 11. Additionally, the molar concentration of each reacting species in Scheme 1 is related to the mass concentration through the corresponding molecular weight.

The Zr residual catalyst in the MetCat HomoPE generated (during chain initiation and branching) a higher concentration of the $R^PO\bullet$ and $R^PO_2\bullet$ radicals than what the Ti residual catalyst did in the Z-N HomoPE. This happened despite that fact that its concentration level (3.5 ppm) was $1/17^{th}$ of Ti (61.0 ppm) in the Z-N HomoPE. The resulting $R^RO\bullet$ and $R^PO_2\bullet$ radicals were consumed during chain propagation and termination that produced higher levels of oxygenated functionalities (including hydroperoxide) and β-hydride elimination products during the high temperature oxidation in the MetCat HomoPE. Therefore, the Zr residual catalyst turned out to be more efficient than the Ti one to (i) cause chain initiation (through the generation of radicals), (ii) decompose the polyethylene hydroperoxide (during chain branching) that otherwise requires considerable activation energy (200 kJ/mol) (Reich L, Stivala S S (1971) Elements of Polymer Degradation, McGraw-Hill, New York; Zweifel H, Maier R D, Schiller M (2009) Plastics Additives Handbook, Hanser Verlag, Germany; Reich L, Stivala S S (1969) Autoxidation of hydrocarbons and polyolefins, M. Dekker, New York—incorporated by reference in its entirety), and (iii) eliminate β-hydrogen (by the carbonyl functionalities) from the polymer chain. This higher degradation performance of Zr residual catalyst can be ascribed to the following:

i. The characteristic surface chemistry and structure that show stronger Lewis acidity and suppression of steric hindrance by the Zr residual catalyst. See Z values (Table 3).
   ii. The electronic configurations of Zr and Ti are [Ar] $3d^24s^2$, and [Kr]$4d^25s^2$, respectively. The atomic radius for Zr is 160 pm and that for Ti is 140 pm. Accordingly, Zr will be more thermally energized than Ti (Roy P K, Surekha P, Raman R, Rajagopal C (2009) Polym Degrad Stab 94:1033-1039; Xu Y-H, Zeng Z-X (2008) J Mol Catal A: Chem 279:77-81—incorporated by reference in its entirety).

The unified molecular level concept of surface chemistry and structure well differentiates the influence of the post-polymerization residual catalyst on the high temperature oxidative degradation of polyethylenes in a coherent fashion. Such a concept, combined with the rigorous constitutive kinetic model, is one aspect of the present disclosure.

In this present disclosure, two supported catalysts were prepared: one Ziegler-Natta [$SiO_2$/$Bu_2Mg$/TMOS/$TiCl_4$]; and another metallocene [$SiO_2$/MAO/($^nBuCp)_2ZrCl_2$]. Next, two ethylene homopolymers were synthesized—Z-N HomoPE and MetCat HomoPE—using these catalysts. The surface chemistry and structure of the as-synthesized catalysts were eventually compared with those of the residual catalysts in these polymers. The residual catalysts differed from the corresponding as-synthesized catalysts in terms of particulate dimension, electronic and steric effects, and the ligands surrounding the transition metal center.

Subsequently, the kinetics of high temperature nonisothermal oxidative degradation using the TGA curves of the experimental polymers were modeled with the analytical Horowitz and Metzger model and the rigorous constitutive kinetic model, the latter of which was developed in the present disclosure. For both polymers, the latter model well fitted to the entire TGA curve while the Horowitz and Metzger model showed appreciable discrepancy. Therefore, the values of the kinetic parameters (n, $E_a$ and Z) estimated by the rigorous constitutive model were much more accurate. The overall reaction order n in each case, as per this model, equaled to 1, despite difference in polymer molecular weight and polydispersity index. Therefore, the proposed unified molecular level concept of surface chemistry and structure of the residual catalysts held all through the degradation process, and random chain scission prevailed.

The rigorous constitutive model-predicted $E_a$ for the decomposition of MetCat HomoPE and Z-N HomoPE turned out to be 122±4.4 and 162±8 kJ/mol, respectively. For both polymers, $E_a$ did not vary as a function of fractional weight loss of the material. These values are much lower than what is required to cleave the polyethylene —C—C— bond (262 to 348 kJ/mol) and the —O—O— bond (200 kJ/mol). Therefore, the residual catalysts caused the thermooxidative degradation in both polymers. However, the Zr residual catalyst decreased $E_a$ more than the Ti analogue. Consequently, MetCat HomoPE showed to be more degradable than Z-N HomoPE despite the residual Zr level was $1/17^{th}$ of the Ti content. This finding is also supported by the model-predicted frequency factors. The greater the frequency factor, the more the steric hindrance to degradation.

Finally, the model results were analyzed considering the mechanism of degradation that involves the transfer of energy from the excited transition metal to the polymer chain, the hydroperoxide decomposition activation energy, and β-hydrogen elimination from the polymer chains by the carbonyl functionalities. Therefore, the current disclosure presents a rigorous constitutive kinetic model that duly illustrates the influence of the characteristic surface chemistry and structure of the residual catalysts on the high temperature oxidative degradation of polyethylenes. The invariant feature of n and $E_a$ indicates the suitability of the model formulation and the effectiveness of the parameter-estimation algorithm.

The invention claimed is:

1. A method of quantitatively determining one or more nonisothermal thermooxidative degradation effects of a polyolefin material comprising a residual catalyst, the method comprising:

obtaining a thermogravimetric analysis spectrum of the polyolefin; and determining a nonisothermal thermooxidative degradation property of the polyolefin with a rigorous constitutive kinetic model based on a structure of the residual catalyst in the thermogravimetric analysis spectrum;

wherein the rigorous constitutive kinetic model is $$r = \frac{dW_{fraction}}{dt} = -Z\exp\left[\frac{-E_a}{R}\left(\frac{1}{T} - \frac{1}{T_0}\right)\right]W_{fraction}^n,$$

wherein
r is an overall rate of degradation,
R is universal gas constant,
Ea is apparent activation energy,
T is absolute temperature in K,
$T_0$ is a centering temperature that resides around a mean temperature range of the reaction,
Z is a frequency factor,
n is overall order of degradation, and
$W_{fraction}$ is a post-degradation weight fraction of a sample of the polymer.

2. The method of claim 1, wherein the polyolefin material is an ethylene homopolymer synthesized with a Ziegler-Natta catalyst.

3. The method of claim 2, wherein the polyolefin material is an ethylene homopolymer synthesized with a metallocene catalyst.

4. The method of claim 2, wherein the Ziegler-Natta catalyst comprises silica, dibutylmagnesium, tetramethoxysilane, and titanium tetrachloride in reacted form.

5. The method of claim 3, wherein the metallocene catalyst comprises silica, ($^n$BuCp)$_2$ZrCl$_2$, and methylaluminoxane in reacted form.

6. The method of claim 1, wherein obtaining a thermogravimetric analysis spectrum of the polyolefin material comprises heating the polyolefin material, from room temperature to 600° C. at a rate of 20° C./min.

7. The method of claim 1, wherein $T_0$ is 725° K.

8. The method of claim 1 wherein Ea is 122-162 kJ/mol.

9. The method of claim 1, wherein Z is $1.2 \times 10^{-3}$ to $2.8 \times 10^{-3}$ sec$^{-1}$.

10. The method of claim 1, wherein n is 1.

* * * * *